United States Patent [19]
Cooper

[11] Patent Number: 5,507,175
[45] Date of Patent: Apr. 16, 1996

[54] CYCLING CHILLED MIRROR DEWPOINT HYGROMETER INCLUDING A SAPPHIRE OPTICAL MIRROR

[75] Inventor: Frank G. Cooper, South Huntington, N.Y.

[73] Assignee: Protimeter, Inc., Commack, N.Y.

[21] Appl. No.: 327,460

[22] Filed: Oct. 21, 1994

[51] Int. Cl.$^6$ .................................................. G01N 25/68
[52] U.S. Cl. .............................. 73/29.02; 374/18; 374/20
[58] Field of Search .............................. 73/29.01, 29.02; 374/17, 18, 19, 20

[56] References Cited

U.S. PATENT DOCUMENTS

| | | | |
|---|---|---|---|
| 3,195,344 | 7/1965 | Francisco | 374/20 |
| 3,528,278 | 9/1970 | Sterling | 374/19 |
| 3,623,356 | 11/1971 | Bisberg | 374/20 |
| 3,926,052 | 12/1975 | Bechtel | 374/20 |
| 5,052,818 | 10/1991 | Nishizawa et al. | 374/17 |
| 5,460,450 | 10/1995 | Buck | 374/20 |

FOREIGN PATENT DOCUMENTS

| | | | |
|---|---|---|---|
| 226930 | 9/1968 | U.S.S.R. | 73/29.02 |
| 661485 | 5/1979 | U.S.S.R. | 73/29.02 |
| 819648 | 4/1981 | U.S.S.R. | 374/20 |
| 2036339 | 6/1980 | United Kingdom | 374/19 |

*Primary Examiner*—Hezron E. Williams
*Assistant Examiner*—Daniel S. Larkin
*Attorney, Agent, or Firm*—Peter L. Michaelson

[57] ABSTRACT

A cycling chilled mirror hygrometer is described wherein the mirror employed comprises a sapphire substrate having deposited thereon alternating layers of titanium dioxide and silicon dioxide. The surfaces resulting from the described technology yield a ten fold enhancement over the "theoretically pure" optical surface characteristics achieved with the prior art gold mirrors. Additionally, these devices have provided ideal surface characteristics for 350 degree optical triangulation, thereby permitting greater primary sensor sensitivity at low humidity levels (below −40 Cdp) and the elimination of long term "optical reflective gain" variations due to aging characteristics as compared with the conventional gold mirrors having impurities.

6 Claims, 2 Drawing Sheets

CYCLING CHILLED MIRROR DEWPOINT HYGROMETER INCLUDING A SAPPHIRE OPTICAL MIRROR

FIELD OF THE INVENTION

This invention relates to a cycling chilled mirror dewpoint hygrometer. More particularly, the present invention relates to a chilled mirror hygrometer including a novel sapphire optical mirror which is chilled during operation to form and maintain a layer of dew on its surface for a limited period of time during which a measurement is effected.

BACKGROUND OF THE INVENTION

In recent years, humidity measurements have played an ever increasing role in industrial, laboratory, and process control applications by enhancing the quality of products produced while simultaneously effecting significant economies.

The technology known as "chilled mirror hygrometry" was introduced some three decades ago and has resulted in the most accurate, stable, and repeatable dewpoint measurement instruments to be sold commercially.

In this technology, there is typically employed an optically smooth surface which is continuously cooled by means of a thermoelectric cooling means to a temperature known as the dew point, the temperature at which a sample of air becomes saturated and produces dew or mist. This process involves the lowering of the temperature of a mirror at a precisely controlled rate until the formation of dew is detected. Before the dew so formed is able to form a continuous layer, the mirror is heated and the dew thereon evaporated. Accordingly, the mirror surface is essentially in a dry state and includes a dew layer for a very limited time period during which the dew point measurement is made.

Although this technology has been used successfully for many years, it has been recognized that any retention of a dew layer on a mirror surface tends to encourage airborne contaminants to adhere to the mirror. Such contamination impairs the reflective performance of the mirror, so resulting in the introduction of measurement errors unless a continuous cleansing procedure is employed. Accordingly, workers in the art have continued in their efforts to find new materials and to develop new techniques which tend to reduce mirror contamination.

SUMMARY OF THE INVENTION

In accordance with the present invention, this end has been attained by the use of a novel structured optical mirror comprising electron beam deposited sapphire bearing a coating comprising alternating layers of titanium dioxide and silicon dioxide.

Studies have revealed that the multiple coatings enable broadband reflective characteristics within the useful spectrum of ultraviolet emitter/receiver pairs. The surfaces resulting from the described technology yield a ten fold enhancement over the "theoretically pure" optical surface characteristics achieved with the prior art gold mirrors.

Additionally, these devices have provided ideal surface characteristics for 350 degree optical triangulation, thereby permitting greater primary sensor sensitivity at low humidity levels (below −40 Cdp) and the elimination of long term "optical reflective gain" variations due to aging characteristics as compared with the conventional gold mirrors having impurities.

BRIEF DESCRIPTION OF THE DRAWING

The invention will be more readily understood by reference to the following detailed description taken in conjunction with the accompanying drawing wherein.

DETAILED DESCRIPTION OF THE INVENTION

In the fabrication of a cycling chilled mirror dewpoint hygrometer in accordance with the invention, the first step involves the fabrication of an optically smooth sapphire mirror. This end may conveniently be attained by electron beam deposition of sapphire onto a sapphire substrate. A typical procedure for effecting this end involves selection of a high purity sapphire (99.99% purity) substrate for insertion in a conventional electron beam deposition apparatus. The system may conveniently be operated at 200°C. for a time period of approximately one hour. Thereafter, the substrate so prepared is disposed in an evaporation apparatus having two evaporation materials, namely, titanium oxide and quartz, which are to be deposited upon the sapphire substrate alternatively. An electron beam gun is used to effect evaporation. In practice, it has been found advantageous to initially deposit a thin film of titanium dioxide having a thickness of approximately 109.41 (plus or minus 1%) nanometers on the sapphire substrate followed by approximately 166.31 (plus or minus 1%) nanometers of silicon dioxide. This process is repeated until a stacked structure is prepared having up to 19 layers, the specific number of layers being dictated by considerations relating to reflectance per cent required. Both the top layer and the bottom layer of the stack comprise titanium dioxide. The structure so prepared is now ready for use in the hygrometer shown in FIG. 1.

Figure 1:
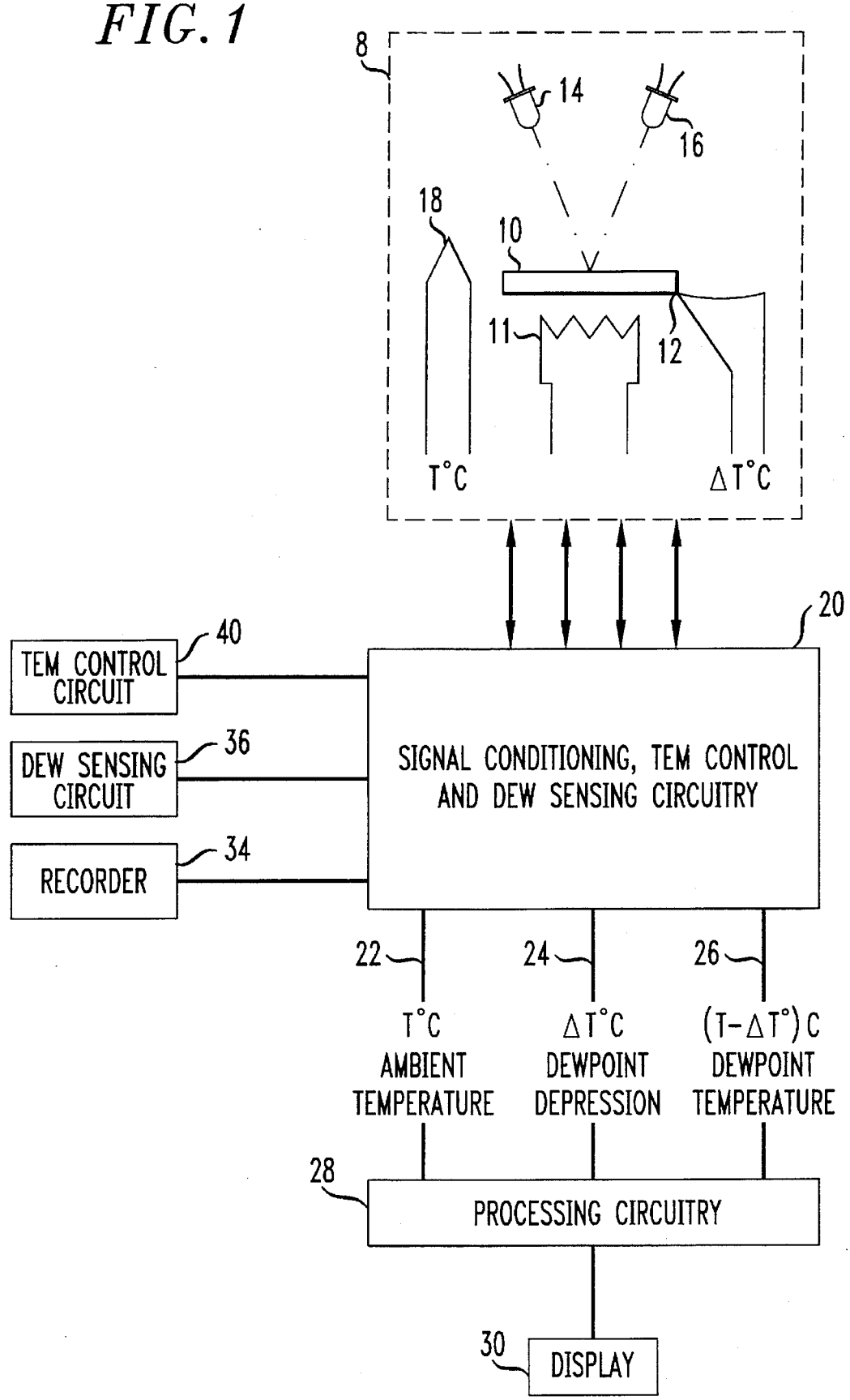
FIG. 1 is a schematic diagram of a conventional chilled mirror hygrometer embodying the sapphire mirror of the invention.

With reference now more particularly to FIG. 1 there is shown an apparatus including a sensor 8 which incorporates sapphire mirror 10, prepared as described, which provides the optically smooth reflective surface, mirror 10 having associated therewith cooling means 11, for example, a thermoelectric cooling means thermoelectric module (TEM) operating in accordance with the Peltlet effect, and also having associated therewith a temperature sensing device 12, such as a thermistor or solid state sensor, or thermocouple in contact with or embedded in mirror 10. A light source 14 is arranged to direct a beam of light on to the surface of the sapphire mirror 10 and an electrical photosensitive device 16, such as a photocell, photodiode or the like is arranged to receive the light from light source 14, after reflection by the reflective surface of body 10. A further temperature sensing device 18, such as a thermistor or solid state sensor, is provided for sensing the ambient temperature (for room relative humidity measurements).

The cooling device, the temperature sensing device, the light source 14 and the photosensitive device 16 are electrically connected with circuitry indicated generally as signal conditioning, TEM control, and dew sensing circuitry 20 for supplying the necessary electrical current to cooling means 11 and the light source 14 and receiving and processing the electrical signals from the thermistors and the photosensitive device 16, the circuitry 20 also being arranged to provide respective output signals on outputs 22, 24 and 26 i.e. ambient temperature (T°C.), dewpoint depression (ΔT°C.), and dewpoint temperature ((T–ΔT) °C.) signals, respectively, which are selectively connectable. By processing the signals appropriately through processing circuitry 28, the respective values may be displayed at display 30.

In the operation of the device, sapphire mirror 10 is cooled gradually below ambient temperature by operation of the cooling means controlled through TEM control circuit 40 until a predetermined change in the level of light detected by device 16 is detected, on reflective surface of mirror 10 by dew sensing circuit 36. During the cooling of the sapphire mirror, the temperature thereof is continuously monitored by means temperature sensing of device 12 and the temperature of the mirror 10, at the time when the predetermined change in the level of light reflected from mirror 10 is attained, is recorded by recorder 34 in the circuitry 20 as the dew point temperature measured in that cycle. Mirror 10 is then permitted to rise in temperature or, alternatively, may be heated. The entire cycle is then repeated, mirror 10 being again gradually cooled until the formation of dew thereon is detected.

Figure 2:
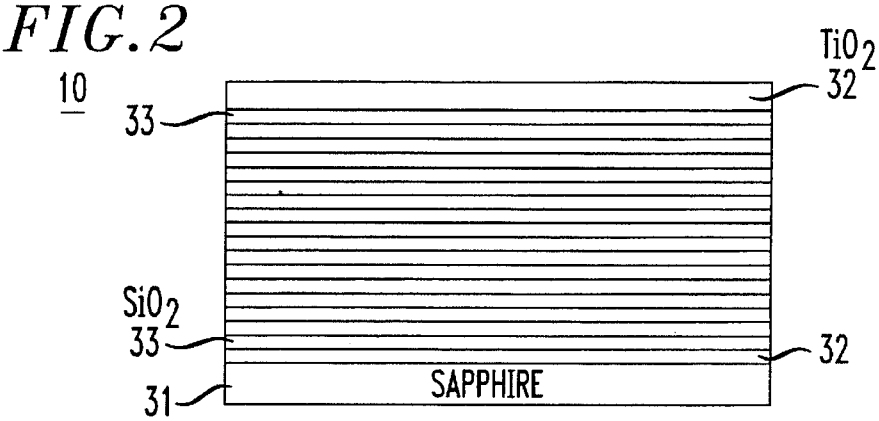
FIG. 2 is a front elevational view in cross-section showing the electron beam deposited sapphire mirror employed in the practice of the invention.

With reference now to FIG. 2, there is shown a front elevational view in cross-section showing sapphire mirror 10 including a sapphire substrate 31 and alternating layers of titanium dioxide 32 and silicon dioxide 33. As indicated, the height of the stacked layers is dependent upon control of the deposition within the tolerances set forth above to yield the desired reflectance. In an exemplary embodiment of the practice of the present invention, a nineteen layer stacked coating comprising alternating titanium dioxide layers of 109.41 nanometers and silicon dioxide coatings of 166.31 nanometers was prepared. The structure so prepared was inserted in an apparatus of the type shown in FIG. 1 and humidity measurements made in a Thunder Scientific Model 2500 humidity chamber.

Figure 3:
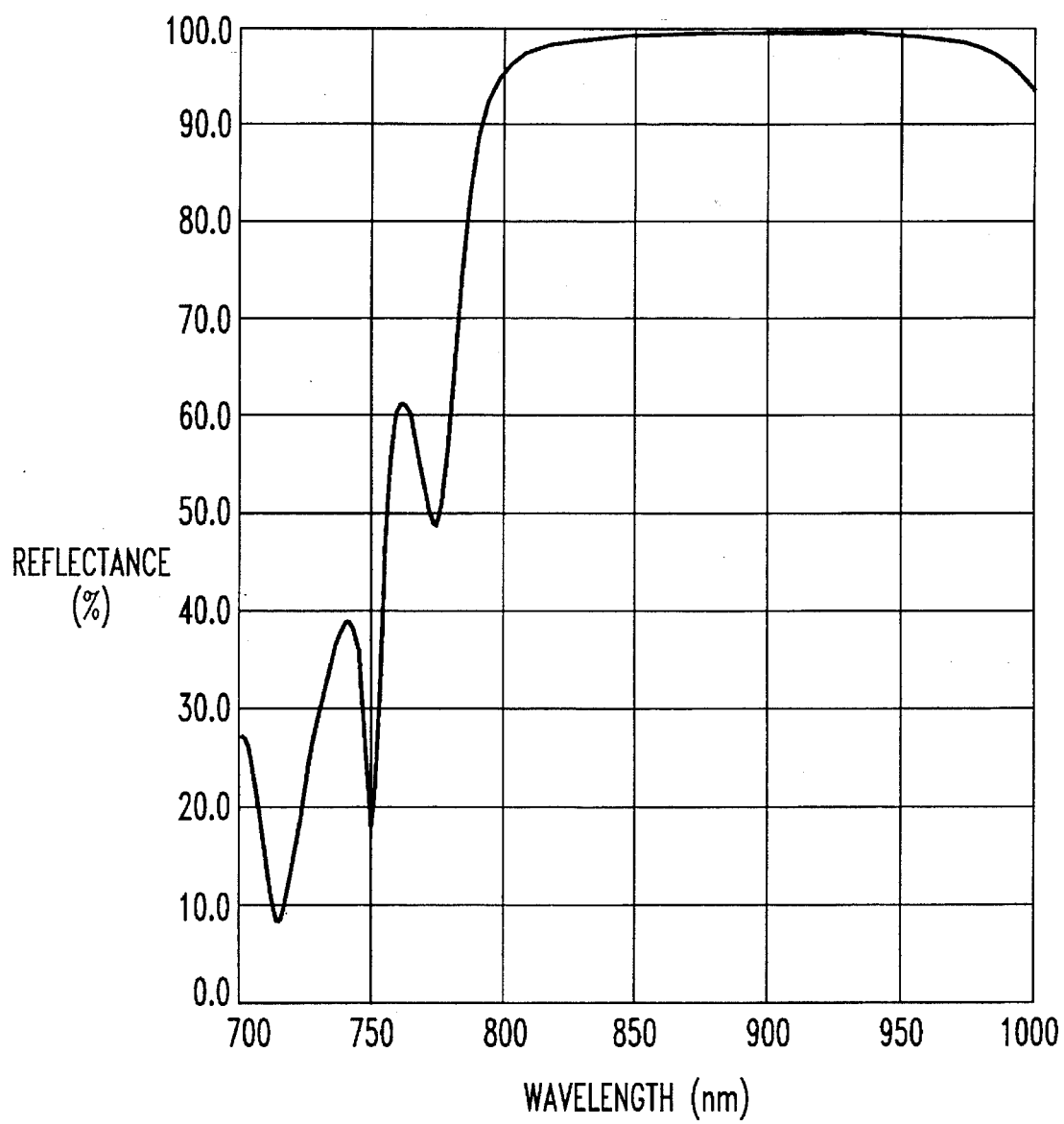
FIG. 3 is a graphical representation showing the reflectance, in percent, against wavelength of incident light resulting from the use of the inventive sapphire mirror.

With reference now to FIG. 3, there is shown a graphical representation on coordinates of reflectance, in percent against wavelength, in nanometers, showing reflectance, as a function of wavelength of incident light, using a sapphire mirror in the device shown in FIG. 1.

While the invention has been described in detail in the foregoing description, it will be understood by those skilled in the art that variations may be made without departing from the spirit and scope of the invention. Thus, for example, the technique chosen for deposition of the sapphire substrate and evaporation of the coating materials thereon may be varied as can the number of coating layers to be deposited. It will be appreciated that processing parameters employed for such techniques will be within the skills of the routine artisan.

What is claimed is:

1. Device for measuring dew point including a cycling chilled mirror comprising a sapphire substrate having deposited thereon alternate layers of titanium dioxide and silicon dioxide.

2. Device in for measuring the dewpoint including a mirror in accordance with claim 1 upon which dew is capable of forming, and comprising cooling means for cooling said mirror, dew sensing means for sensing the formation of dew on a surface of the mirror, temperature sensing means for sensing the temperature of the substrate and means, responsive to said dew sensing means, for effecting repeated cycling means wherein the mirror is gradually cooled until dew is detected on the surface of the mirror, the temperature of the mirror being permitted to rise prior to cooling in a subsequent cycle.

3. Device in accordance with claim 2 wherein the dew sensing means includes a light-directing means for directing a beam of light onto the surface of the mirror and means for detecting scattering of light from the surface thereof due to the formation of dew thereon.

4. Device in accordance with claim 2 wherein the sapphire substrate is of 99.99% purity and the thickness of the titanium dioxide and silicon dioxide layers ranges from 108.32 to 110.50 nanometers and 164.65 to 167.97 nanometers, respectively.

5. Device in accordance with claim 4 wherein titanium dioxide layers are 109.41 nanometers in thickness and the silicon dioxide layers are 166.31 nanometers in thickness.

6. Device for measuring dewpoint in accordance with claim 2 further comprising means for recording, as the dewpoint, the temperature of the mirror at which dew is detected on the surface thereof.

\* \* \* \* \*